(12) United States Patent
Nien et al.

(10) Patent No.: US 11,364,319 B2
(45) Date of Patent: Jun. 21, 2022

(54) AIR PURIFIER AND AIR PURIFYING METHOD

(71) Applicant: Industrial Technology Research Institute, Hsinchu (TW)

(72) Inventors: I-Ling Nien, Hsinchu County (TW); Shou-Nan Li, Nantou County (TW); Meng-Hsuan Lee, Changhua County (TW); Hui-Ya Shih, Hsinchu County (TW); Wen-An Xie, New Taipei (TW); Yen-An Chen, Keelung (TW); Chia-Yen Kuo, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 213 days.

(21) Appl. No.: 16/559,654

(22) Filed: Sep. 4, 2019

(65) Prior Publication Data

US 2020/0397940 A1 Dec. 24, 2020

(30) Foreign Application Priority Data

Jun. 19, 2019 (TW) .................................. 108121253

(51) Int. Cl.
*A61L 9/20* (2006.01)

(52) U.S. Cl.
CPC ............. *A61L 9/20* (2013.01); *A61L 2209/13* (2013.01); *A61L 2209/14* (2013.01)

(58) Field of Classification Search
CPC ... A61L 9/20; A61L 2209/14; A61L 2209/212
See application file for complete search history.

(56) References Cited

U.S. PATENT DOCUMENTS

| 6,589,489 B2 | 7/2003 | Morrow et al. |
| 8,318,084 B2 | 11/2012 | Johnson et al. |

(Continued)

FOREIGN PATENT DOCUMENTS

| CN | 101785872 | 7/2010 |
| CN | 205481326 | 8/2016 |

(Continued)

OTHER PUBLICATIONS

Office Action of China Counterpart Application, dated Jun. 3, 2021, pp. 1-13.

(Continued)

*Primary Examiner* — Kevin Joyner
(74) *Attorney, Agent, or Firm* — JCIPRNET

(57) ABSTRACT

An air purifier and a purifying method are provided. The air purifier includes a housing, a sterilization and ozone-generating unit, a physical filter, a first ozone-removing unit, and a cover. The housing has a sidewall and a bottom surface to define a processing space, wherein an upper end of the housing has an air inlet and the sidewall has an air outlet. The sterilization and ozone-generating unit is disposed in the processing space. The physical filter is disposed in the processing space, extends along the sidewall, and surrounds the sterilization and ozone-generating unit. The first ozone-removing unit is disposed between the physical filter and the sidewall. The cover is openably disposed at the air inlet.

9 Claims, 9 Drawing Sheets

(56) References Cited

U.S. PATENT DOCUMENTS

| | | | | |
|---|---|---|---|---|
| 2005/0123455 | A1* | 6/2005 | Inaba | A61L 9/015 422/120 |
| 2010/0178196 | A1* | 7/2010 | Garner | A61L 2/24 422/4 |
| 2018/0264160 | A1* | 9/2018 | Benedek | A61L 9/046 |

FOREIGN PATENT DOCUMENTS

| | | |
|---|---|---|
| CN | 106123226 | 11/2016 |
| CN | 106461242 | 2/2017 |
| CN | 106855263 | 6/2017 |
| CN | 206320916 | 7/2017 |
| CN | 206387024 | 8/2017 |
| CN | 107441598 | 12/2017 |
| CN | 108224608 | 6/2018 |
| CN | 207963034 | 10/2018 |
| CN | 108895561 | 11/2018 |
| CN | 208139427 | 11/2018 |
| CN | 208704039 | 4/2019 |
| CN | 208886959 | 5/2019 |
| EP | 1891982 | 2/2008 |
| JP | H05322217 | 12/1993 |
| TW | I311489 | 7/2009 |
| TW | M397501 | 2/2011 |
| TW | M457859 | 7/2013 |
| TW | I523826 | 3/2016 |
| TW | M531565 | 11/2016 |
| TW | I633925 | 9/2018 |

OTHER PUBLICATIONS

"Office Action of Taiwan Counterpart Application," dated Sep. 26, 2019, p. 1-p. 9.

Office Action of China Counterpart Application, dated Nov. 11, 2021, pp. 1-14.

Yao Zhongpeng, "Principles, Design and Application of Air Purification", China Science and Technology Press, Sep. 2014, with English translation thereof, pp. 1-15.

USEPA, "Guide to air cleaners in the home.", EPA Indoor Environments Division, Jul. 2018, pp. 1-7.

Jui-Hsuan Yang et al., "Effectiveness of an ultraviolet-C disinfection system for reduction of healthcare-associated pathogens.", Journal of Microbiology, Immunology and Infection, vol. 52, No. 3, Jun. 2019, pp. 487-493.

Ameer Megahed et al., "The microbial killing capacity of aqueous and gaseous ozone on different surfaces contaminated with dairy cattle manure.", PLOS (Public Library of Science) ONE, May 14, 2018, pp. 1-22.

Janie D. McClurkin et al., "Half-life time of ozone as a function of air movement and conditions in a sealed container." Journal of Stored Products Research, vol. 55, Oct. 2013, pp. 41-47.

* cited by examiner

AIR PURIFIER AND AIR PURIFYING METHOD

CROSS-REFERENCE TO RELATED APPLICATION

This application claims the priority benefit of Taiwan application serial no. 108121253, filed on Jun. 19, 2019. The entirety of the above-mentioned patent application is hereby incorporated by reference herein and made a part of this specification.

TECHNICAL FIELD

The present disclosure relates to an air purifier and an air purifying method.

BACKGROUND

For the current air purifier, a high efficiency particulate air (HEPA) filters is used to collect bacteria and viruses, and ultraviolet C (UVC) is used for sterilization. However, the above manner has at least the following problems. First, UVC cannot illuminate the entire HEPA filter, so sterilization cannot be effectively performed. Second, UVC may produce a high concentration of ozone, and the generated ozone may be discharged to the outside along with the air, thus causing damage to the human respiratory system.

SUMMARY

The air purifier of the present disclosure includes a housing, a sterilization and ozone-generating unit, a physical filter, a first ozone-removing unit, and a cover. The housing has a sidewall and a bottom surface to define a processing space, wherein an upper end of the housing has an air inlet and the sidewall has an air outlet. The sterilization and ozone-generating unit is disposed in the processing space. The physical filter is disposed in the processing space, extends along the sidewall, and surrounds the sterilization and ozone-generating unit. The first ozone-removing unit is disposed between the physical filter and the sidewall. The cover is openably disposed at the air inlet.

The air purifier of the present disclosure includes a housing, a sterilization and ozone-generating unit, a physical filter, a cover, and an ozone-removing unit. The housing has a sidewall and a bottom surface to define a processing space, wherein an upper end of the housing has an air inlet and the sidewall has a closable air outlet. The sterilization and ozone-generating unit is disposed in the processing space. The physical filter is disposed in the processing space, extends along the sidewall, and surrounds the sterilization and ozone-generating unit. The cover is openably disposed at the air inlet. The ozone-removing unit penetrates through the cover and communicates with the processing space.

The air purifying method of the present disclosure includes the steps of: (a) introducing air from the outside through the air inlet into the processing space for a period of time; (b) stopping the introduction of the air into the processing space and closing the processing space with the cover; (c) turning on the sterilization and ozone-generating unit; (d) turning off the sterilization and ozone-generating unit; and (e) removing ozone generated by the sterilization and ozone-generating unit using the first ozone-removing unit.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG.

FIG.

FIG.

DETAILED DESCRIPTION

Figure 1A:
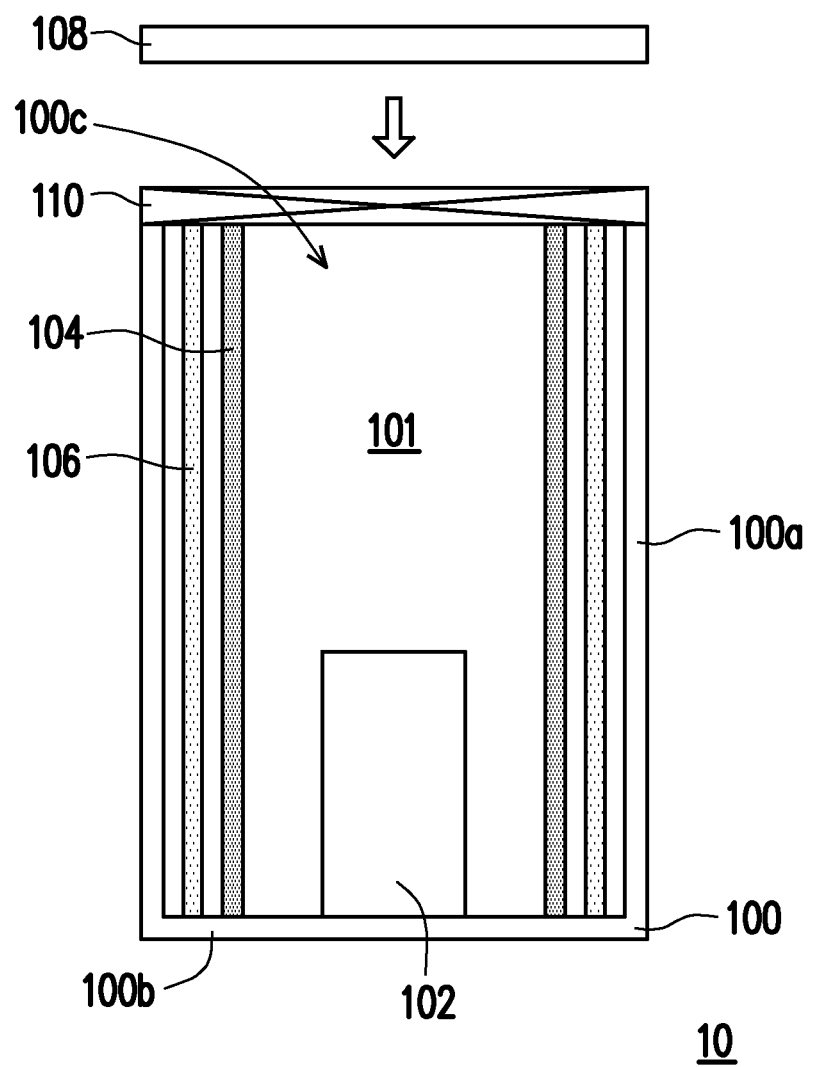
FIG. 1A is a schematic cross-sectional view of an air purifier in accordance with a first embodiment of the present disclosure.

The embodiments are described in detail below with reference to the accompanying drawings, but the embodiments are not intended to limit the scope of The present disclosure. In addition, the drawings are for illustrative purposes only and are not drawn to the original dimensions. For the sake of easy understanding, the same elements in the following description will be denoted by the same reference numerals.

In addition, the terms mentioned in the text, such as "comprising", "including" and "having", are all open-ended terms, i.e., meaning "including but not limited to".

In addition, the directional terms mentioned in the text, such as "on" and "under", are merely used to refer to the drawings and are not intended to limit the present disclosure. Therefore, it is to be understood that "upper" is used interchangeably with "lower", and when an element, such as a layer or a film, is placed "on" another element, the element can be placed directly on the other element or intermediate component. On the other hand, when the component is said to be "directly" placed on the other component, there is no intermediate component between the two.

In the following embodiments, the quantities and shapes are only used to specifically describe the present disclosure in order to understand the contents thereof, and not to limit the present disclosure.

The present disclosure provides an air purifier, wherein ozone is used to sterilize and effectively removed after sterilizing.

The present disclosure provides an air purifying method, wherein after stopping the introduction of air into a processing space of an air purifier, the processing space is closed and ozone is used to sterilize and effectively removed after sterilizing.

Figure 1B:
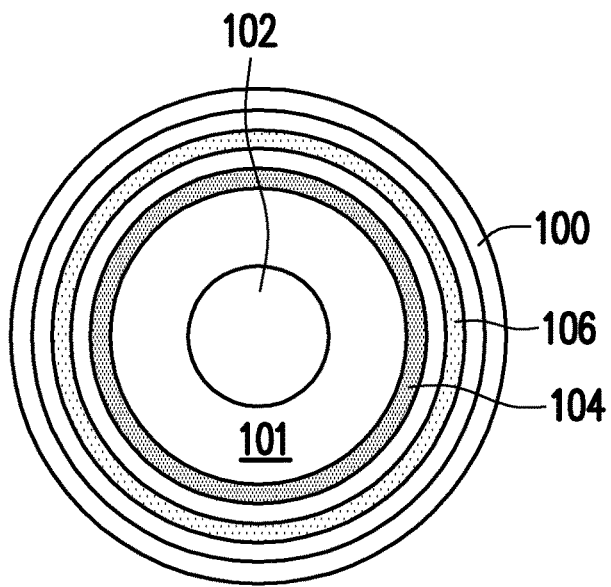
FIG. 1B is a top view of an air purifier in accordance with a first embodiment of the present disclosure.
Figure 1C:
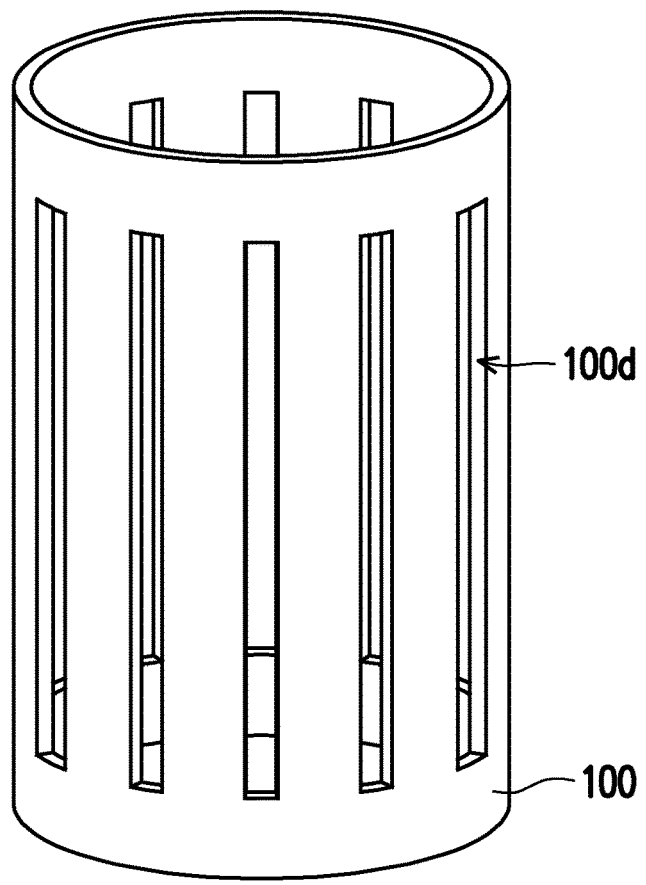
FIG. 1C is a perspective view of a housing of an air purifier in accordance with a first embodiment of the present disclosure.

FIG. 1A is a schematic cross-sectional view of an air purifier in accordance with a first embodiment of the present disclosure. FIG. 1B is a top view of an air purifier in accordance with a first embodiment of the present disclosure. FIG. 1C is a perspective view of a housing of an air purifier in accordance with a first embodiment of the present disclosure.

Referring to FIGS. 1A, 1B, and 1C, an air purifier 10 includes a housing 100, a sterilization and ozone-generating unit 102, a physical filter 104, an ozone-removing unit 106, a cover 108, and a fan 110. The housing 100 has a sidewall 100a and a bottom surface 100b. In the present embodiment, the appearance of the housing 100 is substantially cylindrical, but the present disclosure is not limited thereto. In other embodiments, the appearance of housing 100 may take on any desired shape. Further, an upper end of the housing 100 (the region opposite the bottom surface 100b) has an air inlet 100c, and the side wall 100a of the housing 100 has an air outlets 100d. In FIG. 1C, the number of air outlets 100d is merely exemplary and is not intended to limit the present disclosure.

The sidewall 100a and the bottom surface 100b define a processing space 101. When the air purifier 10 is in operation, air is introduced into the processing space 101 from the outside through the air inlet 100c for purifying. In the present embodiment, the fan 110 is disposed at the air inlet 100c. With the fan 110, outside air can be introduced into the processing space 101. In addition, due to the pressure difference caused by the fan 110, the air entering the processing space 101 does not leak out of the air inlet 100c, but will return to the outside through the air outlets 100d in the sidewall 100a. In other embodiments, the air may also be introduced into the processing space 101 from the outside using manners other than the fan 110, which is not limited by the present disclosure.

The physical filter 104 is disposed in the processing space 101 and extends along the sidewall 100a. In the present embodiment, the physical filter 104 is, for example, a HEPA filter that is disposed along the entire sidewall 100a of the housing 100. When the air entering the processing space 101 flows through the physical filter 104, the physical filter 104 can adsorb viruses, bacteria, suspended particles, and the like in the air.

The ozone-removing unit 106 is disposed between the physical filter 104 and the sidewall 100a. In the present embodiment, the ozone-removing unit 106 is, for example, a carbonized material filter, a catalytic filter, or a combination thereof, or may be any other ozone-removable material or device. The ozone-removing unit 106 can decompose the ozone into oxygen to prevent the ozone in the processing space 101 from reaching the outside through the air outlets 100d and damaging the human body.

The sterilization and ozone-generating unit 102 can sterilize substances adsorbed on the physical filter 104 and can generate ozone. In the present embodiment, the sterilization and ozone-generating unit 102 is, for example, a single UVC device that sterilizes substances adsorbed on the physical filter 104 by UVC, and at the same time, UVC can convert oxygen in the air into ozone. The ozone produced by the sterilization and ozone-generating unit 102 can sterilize the region of the physical filter 104 that is not irradiated by UVC. In the present embodiment, the sterilization and ozone-generating unit 102 is a single component, but the present disclosure is not limited thereto. In other embodiments, the sterilization and ozone-generating unit 102 can include a sterilization device and an ozone-generating device separated from each other. For example, the sterilization device may be a radiation sterilization device, a far infrared sterilization device, a high voltage electric field pulse sterilization device, or a combination thereof, and the ozone-generating device may be an ultraviolet device, a tip discharge device, an electrolysis device, a silent discharge device, an electric ceramic device, photochemical apparatus, or a combination thereof.

The cover 108 is openably disposed at the air inlet 100c. When the cover 108 is capped, the processing space 101 can be substantially sealed, that is, the gas in the processing space 101 does not leak from the air inlet 100c to the outside. In the present embodiment, the cover 108 is an element independent of the housing 100, but the present disclosure is not limited thereto. In other embodiments, the cover 108 may be connected to the housing 100.

The operation of the air purifier 10 of the present embodiment will be further described below.

Figure 2:
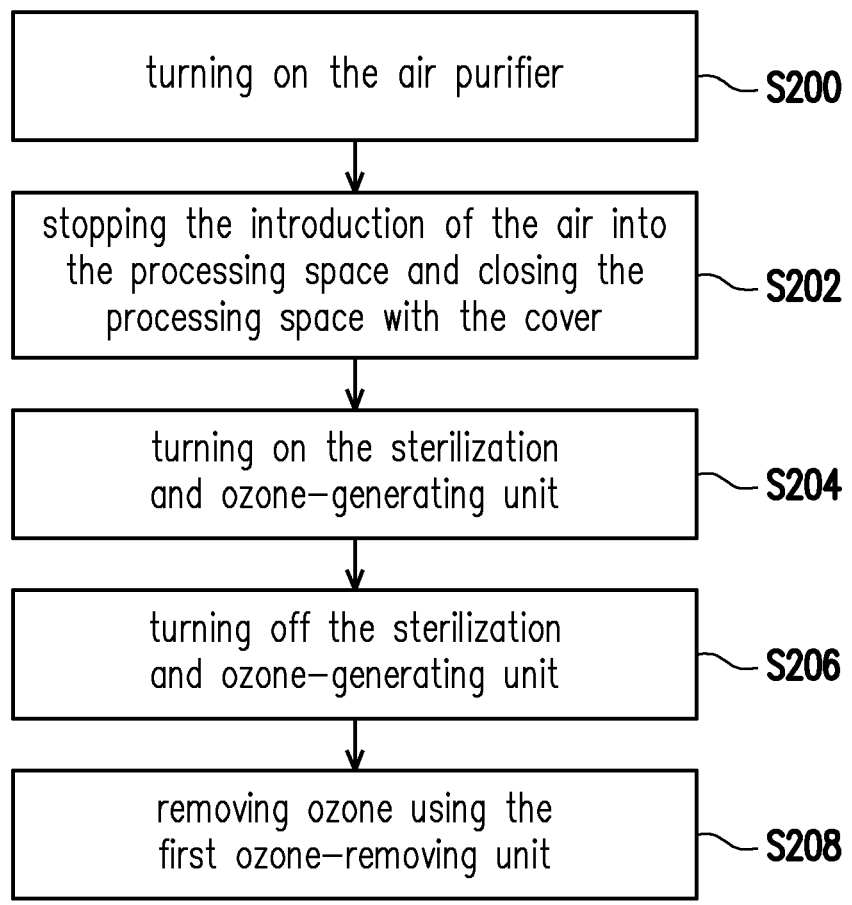
FIG. 2 is a step flow diagram of an air purifying method in accordance with a first embodiment of the present disclosure.

FIG. 2 is a step flow diagram of an air purifying method in accordance with a first embodiment of the present disclosure. Referring to FIGS. 1A, 1B, 1C, and 2, in step S200, the air purifier 10 is turned on, and the air is introduced into the processing space 101 from the outside through the air inlet 100c via the fan 110 for a period of time. In this step, air is continuously introduced into the processing space 101 from the outside, and the air in the processing space 101 continuously passes through the physical filter 104 and is discharged to the outside through the air outlets 100d. The virus, bacteria, and suspended particles in the air are adsorbed on the physical filter 104, so the air discharged to the outside is purified air. After this step is continued for a period of time, the physical filter 104 accumulates a large amount of viruses, bacteria and suspended particles, and therefore must be sterilized.

Next, in step S202, the introduction of air into the processing space 101 is stopped, and the processing space 101 is closed with the cover 108. In the present embodiment, the method of stopping the introduction of air into the processing space 101 is, for example, to stop the fan 110 from operating. The method of stopping the fan 110 may be to directly turn off the power of the fan 110, or to trigger the switch of the fan 110 to turn off the fan 110 when the cover 108 is capped, the present disclosure does not impose any limitation.

Then, in step S204, the sterilization and ozone-generating unit 102 is turned on. When the UVC device is used as the sterilization and ozone-generating unit 102, the UVC can sterilize the irradiated portion of the physical filter 104. In addition, ozone is generated simultaneously. The released ozone can further sterilize the physical filter 104, and in particular, the portion of the physical filter 104 that is not irradiated with UVC can be sterilized. In this way, the entire physical filter 104 can be completely sterilized.

Then, in step S206, after the sterilization is completed, the sterilization and ozone-generating unit 102 is turned off. At this point, the sterilization and ozone-generating unit 102 will no longer produce ozone and the processing space 101 will be filled with previously generated ozone.

Next, in step S208, the ozone-removing unit 106 is utilized to remove ozone generated by the sterilization and ozone-generating unit 102. In this embodiment, the ozone-removing unit 106 is a filter disposed between the physical filter 104 and the side wall 100a, so when the ozone flows through the ozone-removing unit 106, the ozone is decomposed into oxygen, and then oxygen passes through the air outlets 100d in the sidewall 100a and is discharged. In this way, it can effectively prevent the ozone from reaching the outside and damaging the human body.

Thereafter, the cover 108 can be removed and the fan 110 can be returned on to introduce air into the processing space 101 again from the outside through the air inlet 100C, and the above steps are repeated. The method of returning on the fan 110 may be to directly turn on the power of the fan 110, or trigger the switch of the fan 110 to turn on the fan 110 when the cover 108 is removed, and the present disclosure does not impose any limitation.

Figure 3:
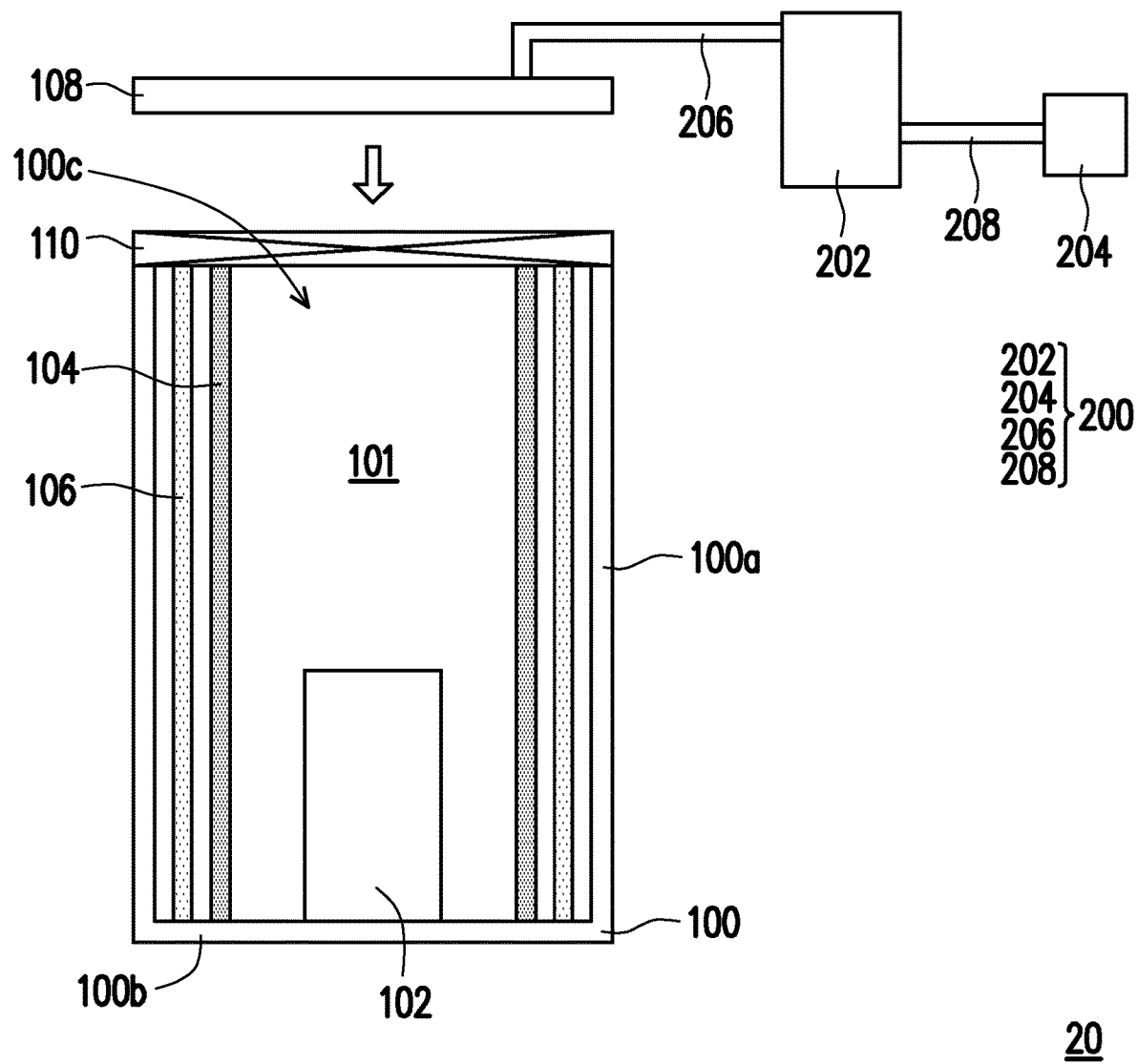
FIG. 3 is a schematic cross-sectional view of an air purifier in accordance with a second embodiment of the present disclosure.

FIG. 3 is a schematic cross-sectional view of an air purifier in accordance with a second embodiment of the present disclosure. In FIG. 3, the same elements as those of the first embodiment will be denoted by the same reference numerals and will not be described again.

Referring to FIG. 3, an air purifier 20 of the present embodiment further includes an ozone-removing unit 200, as compared with the air purifier 10 of the first embodiment. The ozone-removing unit 200 penetrates through the cover 108 and communicates with the processing space 101. In detail, the ozone-removing unit 200 includes an ozone-removing element 202, an air pump 204, a pipe 206, and a pipe 208. The pipe 206 passes through the cover 108 such that the ozone-removing element 202 can communicate with the processing space 101. The pipe 208 communicates with the ozone-removing element 202 and the air pump 204. When the cover 108 is capped, the pipe 206 communicates with the processing space 101 so that the gas can be pumped from the processing space 101 by the air pump 204.

The operation of the air purifier 20 of the present embodiment will be further described below.

In the first embodiment, the ozone in the processing space 101 is removed using the ozone-removing unit 106 disposed between the physical filter 104 and the sidewall 100a as described in step S208 of FIG. 2. In the present embodiment, in addition to the ozone-removing unit 106, ozone is further pumped from the processing space 101 to the ozone-removing element 202 by the air pump 204 to more efficiently remove ozone in the processing space 101. The ozone-removing element 202 may be the same as the ozone-removing unit 106. For example, the ozone-removing element 202 is, for example, a carbonized material filter, a catalytic filter, or a combination thereof, or may be any other ozone-removable material or device. Thereafter, the cover 108 can be removed and the fan 110 can be returned on to introduce air into the processing space 101 again from the outside through the air inlet 100C, and the above steps are repeated.

Figure 4:
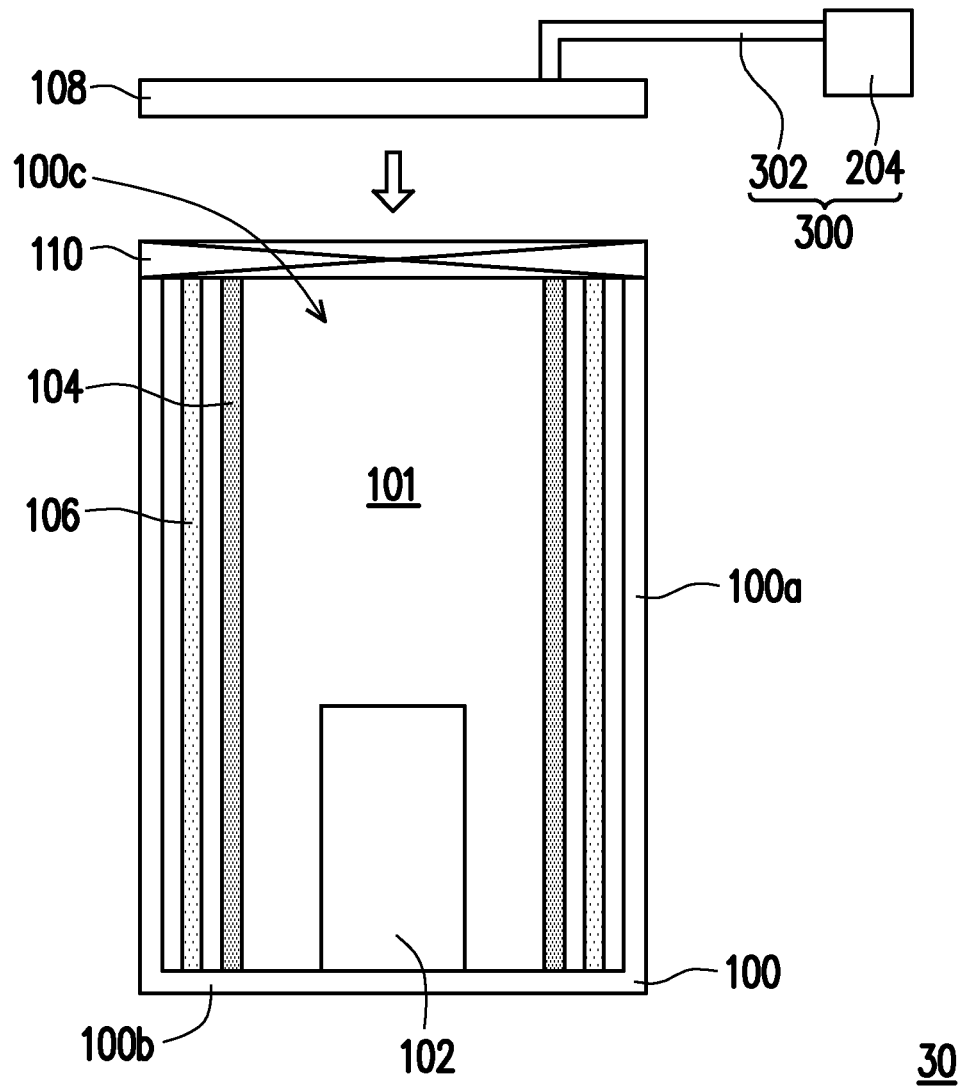
FIG. 4 is a schematic cross-sectional view of an air purifier in accordance with a third embodiment of the present disclosure.

FIG. 4 is a schematic cross-sectional view of an air purifier in accordance with a third embodiment of the present disclosure. In FIG. 4, the same elements as those of the second embodiment will be denoted by the same reference numerals and will not be described again.

Referring to FIG. 4, an ozone-removing unit 300 of an air purifier 30 of the present embodiment includes only the air pump 204 and a pipe 302, as compared with the air purifier 20 of the second embodiment. The pipe 302 is composed of an ozone-removing element. For example, pipe 302 may be comprised of a carbonized material filter, a catalytic filter, or a combination thereof, or may be composed of any other ozone-removable material or device. The pipe 302 passes through the cover 108 such that the air pump 204 can communicate with the processing space 101. When the cover 108 is capped, the pipe 302 communicates with the processing space 101 so that the gas can be pumped from the processing space 101 by the air pump 204.

The operation of the air purifier 30 of the present embodiment is substantially the same as that of the air purifier 20, and details are not described herein again.

Figure 5:
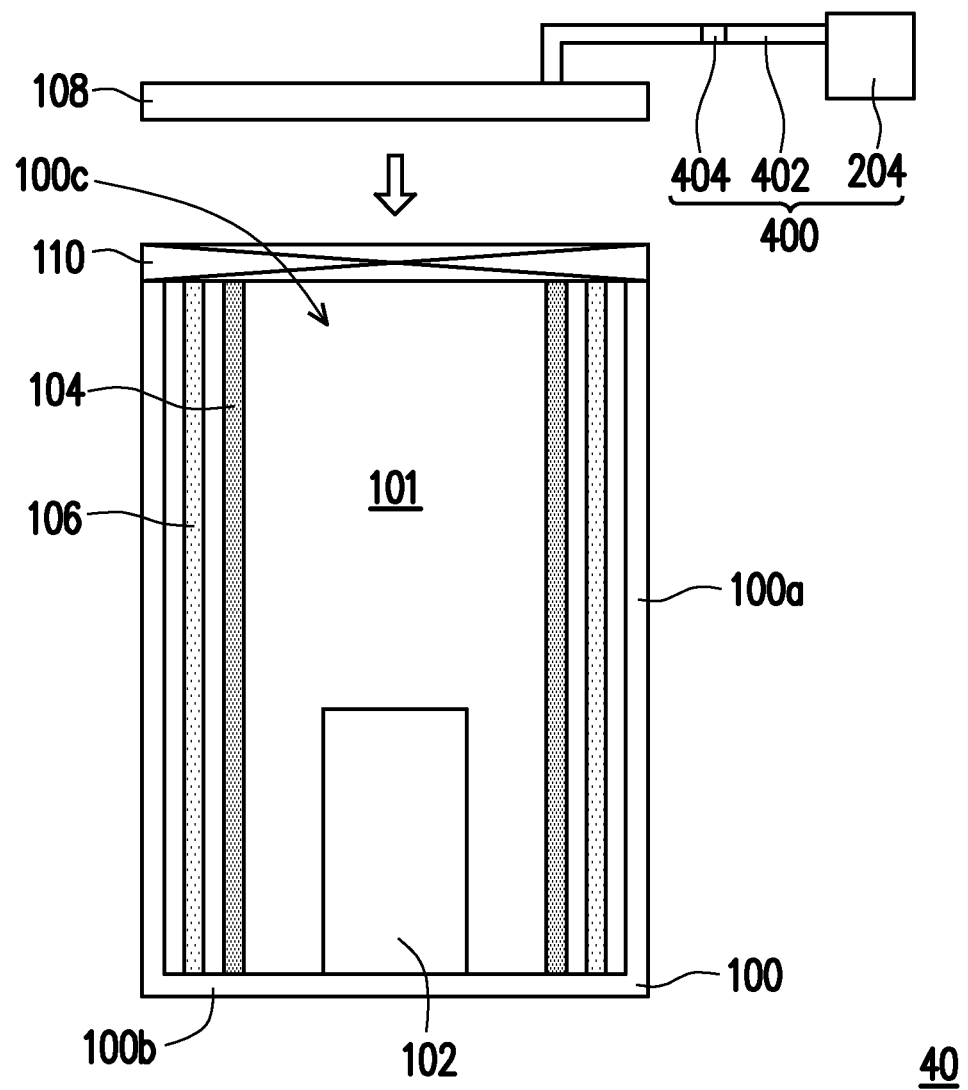
FIG. 5 is a schematic cross-sectional view of an air purifier in accordance with a fourth embodiment of the present disclosure.

FIG. 5 is a schematic cross-sectional view of an air purifier in accordance with a fourth embodiment of the present disclosure. In FIG. 5, the same elements as those of the third embodiment will be denoted by the same reference numerals and will not be described again.

Referring to FIG. 5, in comparison with the air purifier 30 of the third embodiment, in an ozone-removing unit 400 of an air purifier 40 of the present embodiment, a pipe 402 is a pipe generally used for communication, and an ozone-removing element 404 is disposed in the pipe 402. The ozone-removing element 404 is, for example, a carbonized material filter, a catalytic filter, or a combination thereof, or may be composed of any other ozone-removing material or device.

The operation of the air purifier 40 of the present embodiment is substantially the same as that of the air purifier 30, and details are not described herein again.

Figure 6A:
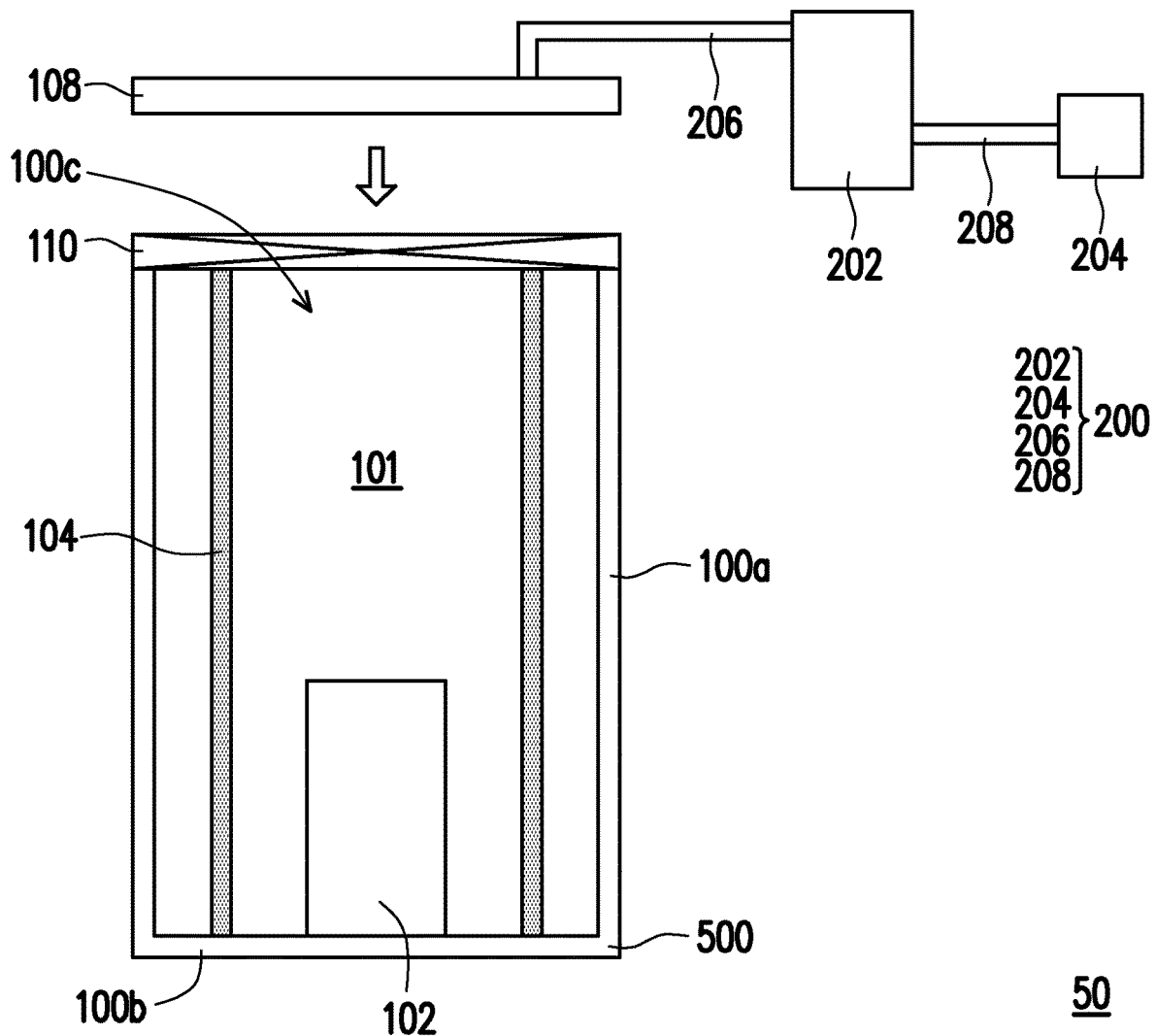
FIG. 6A is a schematic cross-sectional view of an air purifier in accordance with a fifth embodiment of the present disclosure.
Figure 6B:
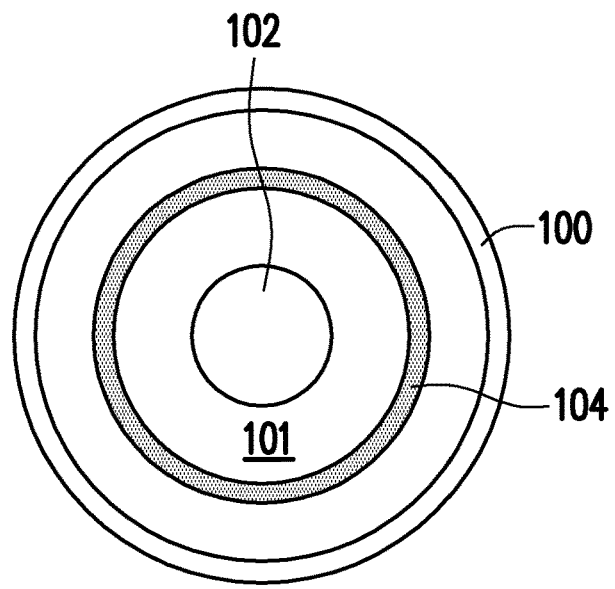
FIG. 6B is a top view of an air purifier in accordance with the fifth embodiment of the present disclosure.
Figure 6C:
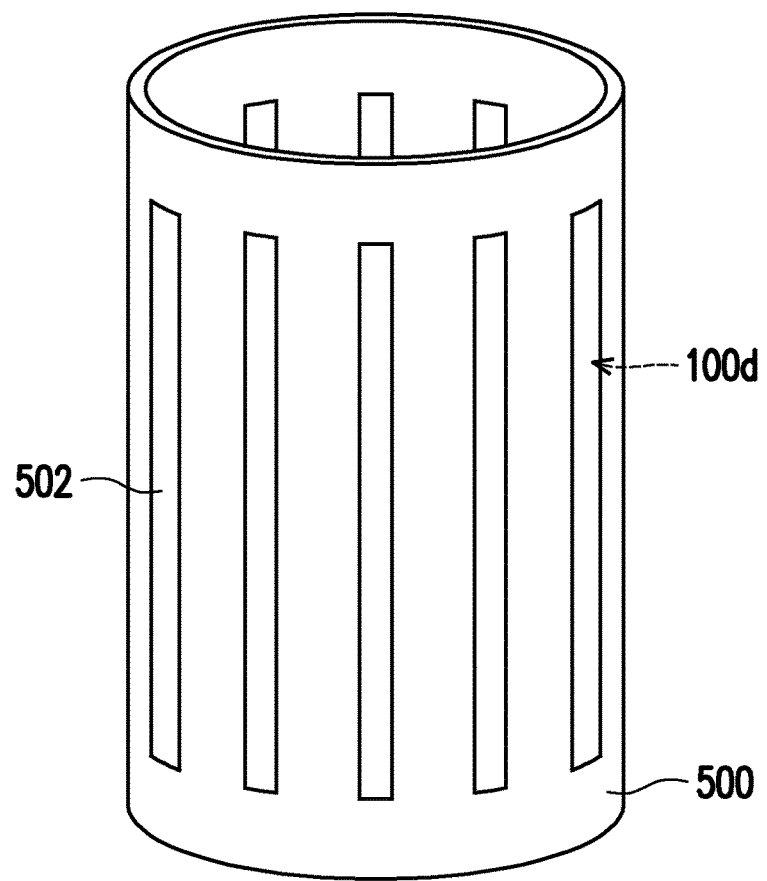
FIG. 6C is a perspective view of a housing of an air purifier in accordance with the fifth embodiment of the present disclosure.

FIG. 6A is a schematic cross-sectional view of an air purifier in accordance with a fifth embodiment of the present disclosure. FIG. 6B is a top view of an air purifier in accordance with the fifth embodiment of the present disclosure. FIG. 6C is a perspective view of a housing of an air purifier in accordance with the fifth embodiment of the present disclosure. In the present embodiment, the same elements as those of the foregoing embodiments will be denoted by the same reference numerals and will not be described again.

Referring to FIGS. 6A, 6B, and 6C, the ozone-removing unit 106 is not disposed in the processing space 101 of an air purifier 50 of the present embodiment, as compared with the air purifier 20 of the second embodiment. That is, in the present embodiment, the ozone-removing process is not performed in the processing space 101. In this way, the air purifier 50 housing 500 must have components to prevent ozone leakage, in order to prevent ozone from reaching the outside through the air outlets 100d and damaging the human body.

In detail, in order to prevent ozone from reaching the outside through the air outlets 100d, the air outlets 100d in the sidewall 100a of the housing 500 must be a closable air outlet. When the purified air is to be discharged to the outside, the air outlets 100d can be opened to allow the purified air to be discharged. When ozone is present in the processing space 101, the air outlets 100d are closed to prevent ozone from being discharged. In the present embodiment, movable baffles 502 are disposed at the air outlets 100d to switch the opening and closing of the air outlets 100d, but the present disclosure is not limited thereto. In other embodiments, the closable air outlet can be set in any manner in the sidewall 100a.

The operation of the air purifier 50 of the present embodiment will be further described below.

Figure 7:
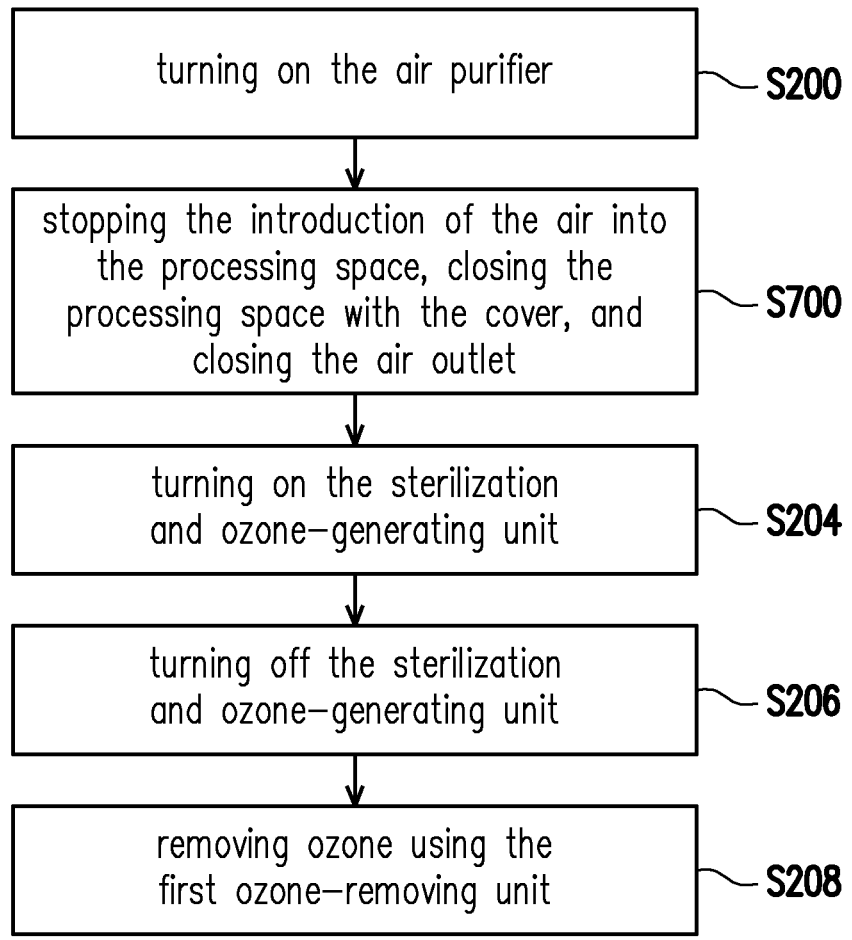
FIG. 7 is a step flow diagram of an air purifying method in accordance with the fifth embodiment of the present disclosure.

FIG. 7 is a step flow diagram of an air purifying method in accordance with the fifth embodiment of the present disclosure. Referring to FIGS. 6A, 6B, 6C, and 7, the operation of the air purifier 50 of the present embodiment is substantially the same as that of the air purifier 20, except that in the present embodiment, when the processing space 101 is closed by the cover 108, the air outlets 100d are closed (step S700) with baffles 502. In this way, it can ensure that ozone will not pass through the air outlets 100d and damage the human body.

In the present embodiment, the ozone-removing unit 200 is used as an external ozone-removing device, but in other embodiments, the ozone-removing unit 200 may be replaced with an ozone-removing unit 300 or an ozone-removing unit 400 as an external ozone-removing device. Furthermore, after the sterilization, the closed air outlets 100d may be opened by removing baffles 502.

Based on the above, the air purifier of the present disclosure includes the sterilization and ozone-generating unit, so that the entire physical filter in the processing space can be effectively sterilized. Further, in the air purifying method of the present disclosure, the introduction of air from the outside into the processing space and the processing space are stopped before the generation of ozone, and after the sterilization, the ozone-removing unit is used to remove the ozone. In this way, it can effectively prevent ozone from being discharged to the outside and damaging the human body.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An air purifier, comprising:
    a housing, having a sidewall and a bottom surface to define a processing space, wherein an upper end of the housing has an air inlet and the sidewall has an air outlet;
    a sterilization and ozone-generating unit, disposed in the processing space;
    a physical filter, disposed in the processing space, extending along the sidewall, and surrounding the sterilization and ozone-generating unit;
    a first ozone-removing unit, disposed between the physical filter and the sidewall;
    a cover, openably disposed at the air inlet; and
    a second ozone-removing unit penetrating through the cover and communicating with the processing space.

2. The air purifier of claim 1, wherein the physical filter unit comprises a high efficiency particulate air (HEPA) filter.

3. The air purifier of claim 1, wherein the sterilization and ozone-generating unit comprises an ultraviolet C (UVC) device.

4. The air purifier of claim 1, wherein the sterilization and ozone-generating unit comprises a sterilization device and an ozone-generating device separated from each other.

5. The air purifier of claim 1, wherein the second ozone-removing unit comprises:
    an ozone-removing element;
    a first pipe, penetrating through the cover to communicate with the processing space and the ozone-removing element;
    an air pump; and
    a second pipe, communicating with the ozone-removing element and the air pump.

6. The air purifier of claim 1, wherein the second ozone-removing unit comprises:
    an air pump; and
    a pipe, communicating with the processing space and the air pump, wherein the pipe is composed of an ozone-removing element.

7. The air purifier of claim 1, wherein the second ozone-removing unit comprises:
    an air pump;
    a pipe, communicating with the processing space and the pump; and
    an ozone-removing element, disposed in the pipe.

8. An air purifying method, suitable for the air purifier of claim 1, comprising:
    (a) introducing air from the outside through the air inlet into the processing space for a period of time;
    (b) stopping the introduction of the air into the processing space and closing the processing space with the cover;
    (c) turning on the sterilization and ozone-generating unit;
    (d) turning off the sterilization and ozone-generating unit; and
    (e) removing ozone generated by the sterilization and ozone-generating unit using the first ozone-removing unit.

9. The air purifying method of claim 8, further comprising:
    after (e),
    removing the cover; and
    performing (a) to (e).

* * * * *